US012533699B2

(12) United States Patent
Hieber et al.

(10) Patent No.: US 12,533,699 B2
(45) Date of Patent: Jan. 27, 2026

(54) DEVICE FOR COATING AN OBJECT WITH A SILICONE COATING

(71) Applicant: Syntegon Technology GmbH, Waiblingen (DE)

(72) Inventors: Walter Hieber, Bühlertann (DE); Steffen Ebert, Crailsheim (DE)

(73) Assignee: Syntegon Technology GmbH, Waiblingen (DE)

( * ) Notice: Subject to any disclaimer, the term of this patent is extended or adjusted under 35 U.S.C. 154(b) by 0 days.

(21) Appl. No.: 18/843,335

(22) PCT Filed: Mar. 1, 2023

(86) PCT No.: PCT/EP2023/055083
§ 371 (c)(1),
(2) Date: Sep. 3, 2024

(87) PCT Pub. No.: WO2023/166012
PCT Pub. Date: Sep. 7, 2023

(65) Prior Publication Data

US 2025/0187029 A1 Jun. 12, 2025

(30) Foreign Application Priority Data

Mar. 2, 2022 (DE) ..................... 10 2022 104 872.1

(51) Int. Cl.
*B05B 12/08* (2006.01)
*A61M 5/315* (2006.01)

(52) U.S. Cl.
CPC ........... *B05B 12/082* (2013.01); *A61M 5/315* (2013.01); *A61M 2207/00* (2013.01)

(58) Field of Classification Search
CPC .. B05B 12/082; A61M 5/315; A61M 2207/00
See application file for complete search history.

(56) References Cited

FOREIGN PATENT DOCUMENTS

| | | | |
|---|---|---|---|
| DE | 19741824 | C2 | 5/2002 |
| EP | 2198974 | B1 | 7/2013 |

(Continued)

OTHER PUBLICATIONS

International Search Report and Written Opinion for Application No. PCT/EP2023/055083 dated Jun. 21, 2023 (14 pages including English machine translation).

(Continued)

*Primary Examiner* — Nathan T Leong
(74) *Attorney, Agent, or Firm* — Michael Best & Friedrich LLP

(57) ABSTRACT

The invention relates to a device (1) for coating an object (2) with a silicone coating (3), the device comprising: at least one processing station (4) having a processing region (5) for receiving the object (2); at least one silicone spray nozzle (6) for applying the silicone (9) to at least one surface region (7) of the object (2) in order to result in a silicone coating (3); at least one optical sensor (8) for monitoring the quality of the silicone coating (3) by identifying silicone (9), wherein the optical sensor (8) has an identification region (10) aligned with the processing region (5), in which identification region the sensor (8) can identify silicone (9); and at least one compressed air nozzle (11), which is aligned with the identification region (10) of the at least one optical sensor (8), for flushing the identification region (10) with compressed air.

12 Claims, 3 Drawing Sheets

(56) References Cited

FOREIGN PATENT DOCUMENTS

| | | | |
|---|---|---|---|
| EP | 3192587 | B1 | 7/2020 |
| GB | 2114024 | A | 8/1983 |
| WO | 2022017808 | A1 | 1/2022 |

OTHER PUBLICATIONS

German Patent Office Action for Application No. 102022104872.1 dated Jun. 10, 2022 (12 pages with English translation).

DEVICE FOR COATING AN OBJECT WITH A SILICONE COATING

BACKGROUND

The invention relates to a device for coating an object with a silicone coating. Objects that should be provided with a silicone coating include ampoules or syringes for medicaments, for example. In particular, silicone coatings are applied to inner surfaces of such ampoules. Silicone coatings serve in particular the purpose that a plunger rod or a plunger slides well and fluid-tightly on the inner surface of the ampoule or syringe. In general, the quality of the silicone coating and, in particular, the completeness thereof is an important parameter, monitoring of which during the production of the coating is desirable or, depending on the product requirement, even necessary.

Identifying silicone during the coating process is advantageous for the monitoring of the silicone coating quality. Silicone is normally applied in the form of a spray mist, which preferably consists of a silicone emulsion and which also contains aqueous constituents. The quality of the silicone coating can be monitored indirectly by monitoring the spray mist which arises during the application of the coating. If the spray mist is incident correctly during the coating process, then it is also possible to assume a sufficient quality of the coating.

Camera-based systems which identify a spray mist made of silicone are conceivable. However, camera-based systems require camera image evaluation for the identification of the spray mist. This is technically quite complex and frequently not realizable in cost-efficient fashion on a large technical scale for the parallel production of a multiplicity of coated objects.

An optical identification of a spray mist using an optical sensor based on an adsorptive effect of the spray mist for light at a specific wavelength is also possible. For example, light can be emitted by a signal source of the sensor and is received by a signal receiver of the sensor. The light is adsorbed in full or in part if a spray mist has formed. Such an optical identification is advantageous in that the evaluation of the signal from the sensor is possible much more efficiently than in the case of a camera-based system. All that needs to be realized for being able to make a statement as to whether or not the spray mist for applying the coating was correctly present is the identification or non-identification of a quantity of light above a threshold value.

The optical identification of a spray mist made of silicone in the interior of an ampoule for the purpose of monitoring the quality of a silicone coating is known from EP 2 198 974 B1, for example.

In principle, all methods for identifying a spray mist are sensitive to disturbances, for example to contamination on camera lenses, signal receivers, signal sources, etc.

SUMMARY

Using this as a starting point, it is an object of the present invention to at least partly solve the problems explained in relation to the prior art. In particular, the intention is to describe a particularly advantageous device for coating an object with a silicone coating, which particularly reliably allows the identification of the formation of a silicone coating.

This object is achieved by the invention in accordance with the features of the disclosure. Attention is drawn to the fact that a person skilled in the art combines the individual features with one another in technologically advantageous fashion and thus arrives at further configurations of the invention.

The invention relates to a device for coating an object with a silicone coating, comprising at least one processing station with a processing region for accommodating the object, at least one silicone spray nozzle for applying the silicone to at least one surface region of the object such that a silicone coating arises, at least one optical sensor for monitoring the quality of the silicone coating by identifying silicone, the optical sensor having an identification region, in which the sensor can identify silicone and which is aligned with the processing region, and at least one compressed air nozzle directed at the identification region of the at least one optical sensor in order to flush the identification region with compressed air.

The device is preferably part of a larger/overarching device for producing or for processing such coated objects. The processing station is preferably one of a plurality of processing stations, at which different steps of the production of such objects are implemented in succession and/or in parallel. The term "processing region" preferably describes spatial regions within the processing station, in which the object is at least intermittently situated during the processing (the application of the coating in this case). The term "identification region" preferably denotes spatial regions monitored by the optical sensor or spatial regions in which optical changes (e.g. the presence of the object, the presence of silicone and/or the presence of water or contamination) lead to changes that can be registered by the optical sensor. By preference, the identification region and the processing region overlap at least in portions such that the formation of the silicone coating occurs both in the processing region and in the identification region and is identified by the optical sensors.

The described device is distinguished in that the identification region is flushed with compressed air. This improves the identification accuracy for silicone. In this case, the term "identification accuracy" refers to an accuracy or a reliability with which a correct/desired embodiment of a silicone coating is distinguished from an incorrect (for example incomplete) embodiment of a silicone layer. The compressed air serves the purpose of flushing or removing contamination and in particular water, which is not part of the silicone coating or the silicone spray mist, from the identification region. This can prevent contamination and in particular water present from bringing about an incorrect identification of silicone. Flushing the identification region with compressed air allows the identification of silicone to be substantially improved.

For example, water may originate from preceding processing steps for the object and may have remained on the object. For example, a station for cleaning/flushing the object with water may be arranged upstream of the device. Water from this cleaning step may have remained on the object. In general, the described device is suitable for applications in humid environments in particular. The identification or the monitoring of the coating with silicone is improved by flushing the identification region with compressed air, even in humid environments.

It is particularly advantageous if the silicone spray nozzle is arranged on a base of the processing station and directed upward such that silicone is able to be sprayed into the processing region from below by means of the silicone spray nozzle, the processing station having guide means for the relative movement between the processing station and the object, in such a way that the silicone spray nozzle is introducible into a cylindrical body of the object through an open end in order to coat an inner surface of the object with silicone.

In particular, the object is an ampoule or a syringe with a cylindrical body and an open end, with the device serving to coat the inner surface of the syringe or ampoule with silicone.

The silicone is preferably provided in the form of an emulsion by the silicone spray nozzle, the emulsion preferably containing water and optionally forming an aerosol together with air. A spray or a mist of silicone or silicone emulsion particularly preferably emerges from the silicone spray nozzle.

The silicone coating on the inner surface of an ampoule should in particular improve the dynamic friction for a plunger or a plunger rod in the ampoule and in the process optionally also contribute to the seal between the inner surface of the ampoule and the plunger or plunger rod.

Ampoules or syringes as objects to be coated may for example have volumes of between 1 mg [milligram] and 100 mg [milligrams]. However, in principle the described method is applicable for coating and monitoring of the coating process for objects of very different sizes. The ampoule preferably has a closed end opposite the open end; however, this closed end is preferably not completely closed off but has an outlet there for fluid (in particular medicament) contained in the ampoule, the diameter of said closed end being very much smaller than the diameter of the cylindrical body. The open end is preferably surrounded by a collar which, starting from the cylindrical body, extends outwardly around the open end, the ampoule optionally being able to be held or clamped at said collar.

The guide means can be configured to lead the processing station or the base to the object from below and/or can be configured to lead the object to the processing station or the base from above.

It is also advantageous if guide means for introducing the object into the processing station are configured to bring about a guided movement of the object through the processing region, during which a distance of the object from a base of the processing station is changed continually during a process of spraying silicone using the silicone spray nozzle in order to bring about a uniform application of the silicone coating on the at least one surface region of the object.

By preference, the device or the processing station is configured such that a relative position between the object and the identification region is modified during a guided movement. Thus, different portions or regions of the silicone coating in the identification region can be monitored by the sensor during the guided movement. By preference, the position of the object relative to the at least one compressed air nozzle is also modified during the guided movement. By preference, the at least one compressed air nozzle is formed stationarily relative to the sensor or the identification region such that relative to the object the at least one compressed air nozzle is moved together with the identification region during the guided movement.

Moreover, it is advantageous if the at least one optical sensor is arranged above a base of the processing station to the side of the processing region, and the identification region is aligned at least partly horizontally for the purpose of identifying silicone in the processing region.

It is also advantageous if the at least one optical sensor has a two-part form with a sensor transmitter and a sensor receiver, the processing region being arranged between the sensor transmitter and the sensor receiver and the identification region having a linear form from the sensor transmitter to the sensor receiver and extending through the processing region.

By preference, the identification region can be understood to be an (imaginary) channel or a measurement path from the sensor transmitter to the sensor receiver. The diameter of the identification region is preferably larger than 1 mm [millimeter] and smaller than 5 mm, for example approx. 2 mm. The diameter of the identification region thus is smaller than the object. By preference, only a region of the object is monitored by the sensor for the purpose of identifying the correct embodiment of the silicone coating. By preference, this region is representative for the embodiment of the silicone coating on the object overall.

By preference, the sensor transmitter is a light source and, in particular, a light source for laser light or a special light-emitting diode (LED). By preference, the sensor receiver is a photosensitive cell for receiving the light or laser light.

Moreover, it is advantageous if the at least one optical sensor is configured to identify light at a wavelength in a range between 400 nanometers and 800 nanometers.

Furthermore, it is advantageous if the at least one optical sensor is configured to identify water components in silicone.

Water can be reliably identified using light in the aforementioned wavelength range. If water is present, light in this wavelength range is adsorbed and a sensor receiver of the sensor receives less light emitted by the sensor transmitter.

Moreover, it is advantageous if the at least one compressed air nozzle is arranged above a base of the processing station to the side of the processing region and directed at the identification region of the at least one optical sensor.

This alignment of the at least one compressed air nozzle allows the identification region to be freed from contamination (in particular from water) in a targeted manner. The compressed air from the compressed air nozzle flushes water out of the identification region in particular, with the result that water in the silicone or the silicone emulsion is identified by the optical sensor, and this identification is not disturbed by other water components (present in the identification region independently of the silicone). The result of the evaluation of the optical sensor signals allows better conclusions to be drawn about the correct embodiment of the silicone layer for this reason.

The device is further advantageous if at least one compressed air nozzle is directed at at least one sensor component of the optical sensor.

In particular, this can also assist with cleaning of surfaces of the optical sensor.

Moreover, it is advantageous if at least two opposing sensor components are arranged above a base of the processing station to the side of the processing region, the processing region being arranged between the sensor components and the device having at least two compressed air nozzles, with a respective compressed air nozzle being fastened to a mount of one of the sensor components and being directed at another one of the sensor components.

In this case, one sensor component is preferably the above-described sensor transmitter and the other sensor component the above-described sensor receiver. However, this may also relate to other sensor components, for example sensors operating independently of one another.

As a result of the structure with compressed air nozzles directed at sensor components arranged on other mounts, the compressed air nozzles in each case flush the sensor components on the other mount. Especially water deposits (water droplets) on a sensor component can thus be removed by compressed air. Thus, an identification region between two sensor components of an optical sensor can be completely freed from contamination (in particular from water).

For example, the mounts can be manufactured from one material throughout, for example from plastic. Channels for compressed air for supplying the compressed air nozzles are preferably integrated in the mount. The compressed air nozzles are preferably in the form of outlet openings. By preference, a plurality of compressed air nozzles are supplied with compressed air by way of a common compressed air source. The compressed air source is preferably connected to the compressed air nozzles via channels.

The intention is also to describe a method for operating the above-described device in this case, the method including the following steps:

a) cleaning the at least one optical sensor using compressed air from the compressed air nozzle;
b) introducing an object into the processing region;
c) cleaning the object using compressed air from the compressed air nozzle;
d) applying the silicone coating to at least one surface region of the object, silicone of the silicone coating being provided by means of the at least one silicone spray nozzle;
e) monitoring the quality of the silicone coating using the at least one optical sensor by identifying silicone during and/or after step d).

It should be pointed out that the particular advantages and configuration features mentioned in the context of the above-described device are also applicable and transferable to the method described below.

This is particularly advantageous if water on the optical sensor and on the object is removed in step a) and step c) using the compressed air from the compressed air nozzles and wherein the optical sensor identifies water components in the silicone in step e).

The device and the method are preferably configured for a permanent provision of compressed air from the compressed air nozzles. Compressed air flows permanently out of the compressed air nozzles. Accordingly, steps a) and c) are preferably implemented by a constant (uninterrupted) emergence of compressed air from the compressed air nozzles. For as long as the object has not yet been introduced into the processing region (in step a)), the compressed air is preferably incident on the optical sensor or its components and removes contamination (in particular water) from the sensor or the sensor components. As soon as the object has been introduced into the processing region (after step b)), the compressed air is incident on surfaces of the object and removes contamination (in particular water) from these surfaces. Monitoring the quality of the silicone coating (step e)) is preferably implemented at least partially in parallel with the formation of the silicone coating according to step d). This is preferably implemented by virtue of the formation of the silicone spray provided to apply the silicone coating using the silicone spray nozzle being sensed during step e). By preference, the object is removed from the processing region again after steps d) and e) (step f)). Preferably, this is followed by a further implementation of the described method steps with a further object intended to be coated with silicone.

By preference, the guided movement already described above in the context of the device which modifies the position of the object relative to the identification region, the sensors and the compressed air nozzles is implemented during step d) and e), and so the formation of the silicone coating is implemented over a specified surface region of the object and can be monitored.

By preference, implementing method steps a) to e) is also preceded by a calibration of the sensor which takes place using objects to be coated, the sensor and/or a controller configured to evaluate the sensor signals being calibrated on the basis of objects. In this case, there preferably is a calibration with coated objects, the coating of which was assessed as suitable or acceptable in a separate examination.

Particularly preferably, the calibration comprises the ascertainment of a plurality of measurement values using the sensors (for example from a plurality of different objects). By preference, at least one mean value is formed from a plurality of measurement values of the sensors during the calibration, and this mean value represents a reference value. Particularly preferably, a plurality of measurement values are likewise captured during step e) or during step d).

By preference, the evaluation of the measurement values captured during step e) is implemented by a comparison with a reference value. In embodiment variants, this comparison can be implemented by a subtraction of the measurement values captured during step e) from the mean value.

Particularly preferably, the method and the controller of the device are also configured to execute evaluation routines which, in terms of time, extend over a plurality of coating processes for a plurality of objects.

For example, there can be an evaluation of the amount of silicone processed, within the scope of which the measurement values captured during a plurality of coating processes are added.

In preferred embodiment variants, the calibration additionally comprises reference measurements taken at different volumetric flow rates of the compressed air emerging from the compressed air nozzles. By preference, a volumetric flow rate of the compressed air which brings about sufficient flushing of the identification region is ascertained such that the silicone coating quality can be monitored using the at least one optical sensor, with an acceptable compressed air consumption being set at the same time. By preference, the device has compressed air flow setting means to this end, by means of which the compressed air flow can be set.

BRIEF DESCRIPTION OF THE DRAWINGS

The invention and the technical context of the invention are explained in detail below on the basis of the figures. The figures show preferred exemplary embodiments, which do not restrict the invention. In particular, attention should be drawn to the fact that the figures and, in particular, the proportions depicted in the figures are only schematic. In detail.

DETAILED DESCRIPTION

Figure 1:
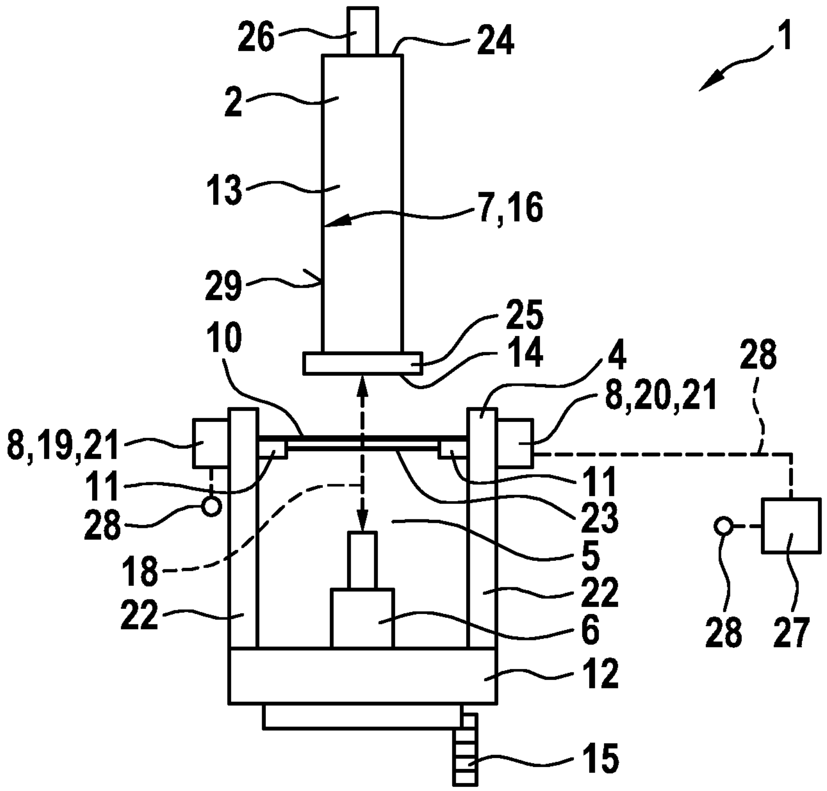
FIG. 1: shows a described device in a state prior to the introduction of an object to be coated.

FIGS. 1 to 4 show the device 1 described herein in different states, and these figures are described together herein. The device 1 for applying a silicone coating 3 to an object 2 is illustrated. The object 2 preferably is an ampoule or a syringe having a cylindrical body 13, an interior, an open end 14 via which the interior is accessible and a closed end 24 which preferably also still includes an outlet 26. The open end 14 is preferably also surrounded by a collar 25. The silicone coating 3 should be applied to an inner surface 16 of the object 2 and it serves the purpose that a plunger (not illustrated here) and/or a plunger rod attached to the plunger moves easily in the object 2. The inner surface 16 thus forms a surface region 7 of the object 2, on which the silicone coating 3 should be formed. Optionally, the surface region 7 to be coated does not form the entire inner surface 16 of the object 2 to be coated. In preferred embodiment variants, (only) the regions of the inner surface 15 on which the plunger or plunger rod (not depicted here) should slide easily are provided with the silicone coating 3.

The device 1 has a processing station 4, in which the silicone coating 3 is applied. To this end, the object 2 must be introduced into a processing region 5 of the processing station 4. The processing station 4 preferably has a base 12 where a silicone spray nozzle 6 is situated, the latter being configured to spray silicone 9, for example in the form of an emulsion, on a surface region 7 of the object 2 in order to form the silicone coating 3. The silicone spray nozzle 6 is preferably directed such that the silicone 9 is sprayed upwardly. The object 2 is introduced into the processing station 4 from above such that an open end 14 of the object 2 is directed downward, and the silicone spray nozzle 6 sprays the silicone 9 through the open end 14 on an inner surface 16 of the object 2 in order to form the silicone coating 3 there.

The process of applying the silicone coating 3 to the surface regions 7 of the object 2 is monitored by optical sensors 8 which are arranged on the processing station 4. The optical sensors 8 depicted in the figures are each embodied in two parts with two sensor components 21, specifically with a sensor transmitter 19 and a sensor receiver 20. The sensor transmitter 19 and the sensor receiver 20 are arranged such that the processing region 5 is arranged between the sensor transmitter 19 and the sensor receiver 20. An identification region 10 in which the optical sensor 8 configured thus identifies silicone 9 is a region between the sensor transmitter 19 and the sensor receiver 20. The sensor transmitter 19 transmits signals (by preference light at a defined wavelength or in a defined wavelength range) received by the sensor receiver 20. The signals transmitted by the sensor transmitter 19 are influenced by the presence of silicone 9 in the identification region 10. This influence can be identified by a controller 27 which is connected to the sensor transmitter 19 and the sensor receiver 20 by way of data lines 28 or by way of signal lines. Optionally, the controller 27 has calibration data for this purpose, the calibration data having been ascertained previously by the optical sensor 8 during calibration measurements.

Moreover, compressed air nozzles 11 are preferably arranged on the processing station 4. The compressed air nozzles 11 are directed at the identification region 10 of the optical sensors 8. The identification region 10 is flushed with compressed air emerging from the compressed air nozzles 11. This cleans the identification region 10 and components arranged in the identification region 10. In particular, residual water is removed from the identification region 10 by flushing with compressed air. Silicone 9 is preferably identified using the optical sensor 8 by virtue of the fact that water constituents in the silicone 9 are identified by the optical sensor 8. It is for this reason that residual water in the identification region 10 which is not water constituents of the silicone 9 interferes with the measurement of silicone 9 using the optical sensor 8. The removal of such residual water by flushing with compressed air thus improves the identification accuracy of the silicone 9 using the optical sensor 8.

In the embodiment variant of the device 1 according to FIGS. 1 to 4, the sensor components 21 of the optical sensor 8 (the sensor transmitter 19 and the sensor receiver 20) are each fastened to mounts 22 which, starting from the base 12 with the silicone spray nozzle 6, extend upwardly to the side of the processing region 5 such that the processing region 5 is arranged between the sensor components 21 and an identification region 10 of the optical sensor 5 extends through the processing region 5. Arranged on each of the mounts 22 is at least one respective compressed air nozzle 11, the latter being directed into the identification region 10 and the processing region 5 and at the respectively other mount 22 or the respectively other sensor component 21 and the respectively other compressed air nozzle 11 on the other mount 22.

FIG. 1 depicts a situation prior to the introduction of the object 2 into the processing region 5. Silicone 9 is not yet provided by the silicone spray nozzle 6. However, flushing with compressed air from the compressed air nozzles 11 is already taking place. The compressed air flowing out of the compressed air nozzles 11 is now incident on the opposing sensor component 21 of the optical sensor 8 in each case. For this reason, the compressed air flushes away residual water on the respective sensor component 21.

Figure 2:
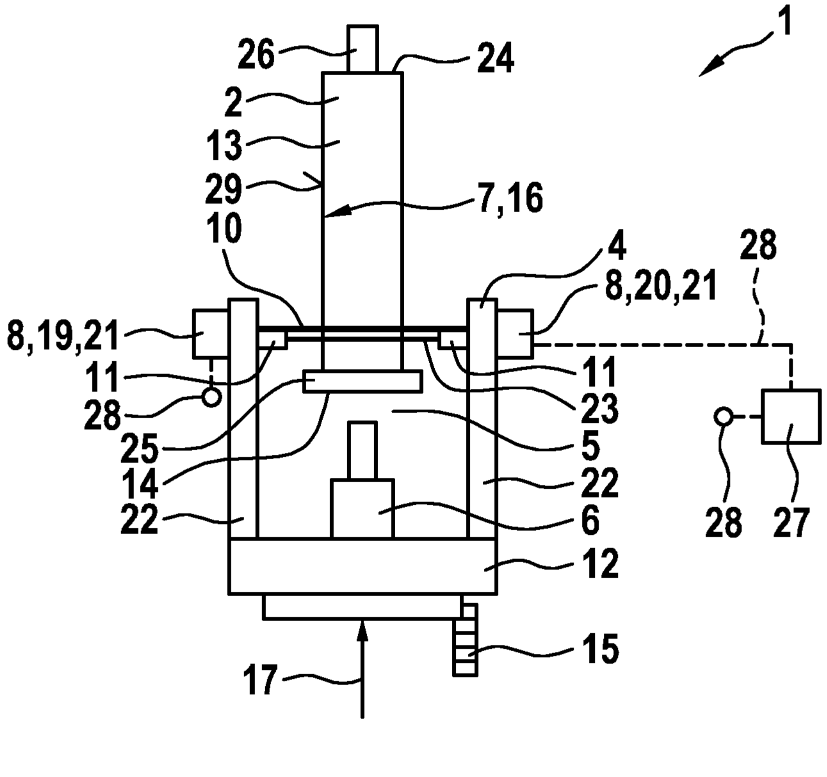
FIG. 2: shows a described device during the introduction of an object to be coated.

FIG. 2 depicts a situation in which the object 2 is moved into the processing region 5; it occurs after the situation in FIG. 1. To this end, the distance 18 between the processing station 4 or the base 12 of the processing station 4 is reduced. This can be implemented by a guided movement 17 of the object 2 toward the processing station 4 and/or a guided movement 17 of the processing station 4 toward the object 2. Guide means 15, which may e.g. comprise a drive for moving the processing station 4, are depicted schematically in FIGS. 1 to 4. During the guided movement 17, the object 2 reaches into the processing region 5 and also into the identification region 10. The compressed air emerging from the compressed air nozzles 11 is incident on an outer surface 29 of the object 2 and thus flushes away residual water on the outer surface 29 of the object 2. Thus, residual water on the sensor components 21 (as per FIG. 1) and residual water on the outer surface 29 of the object 2 (as per FIG. 2) are preferably removed. For this reason, the optical sensor 8 is able to perform a much better identification of water components in the silicone 9 applied to the inner surface 16 of the object 2.

Figure 3:
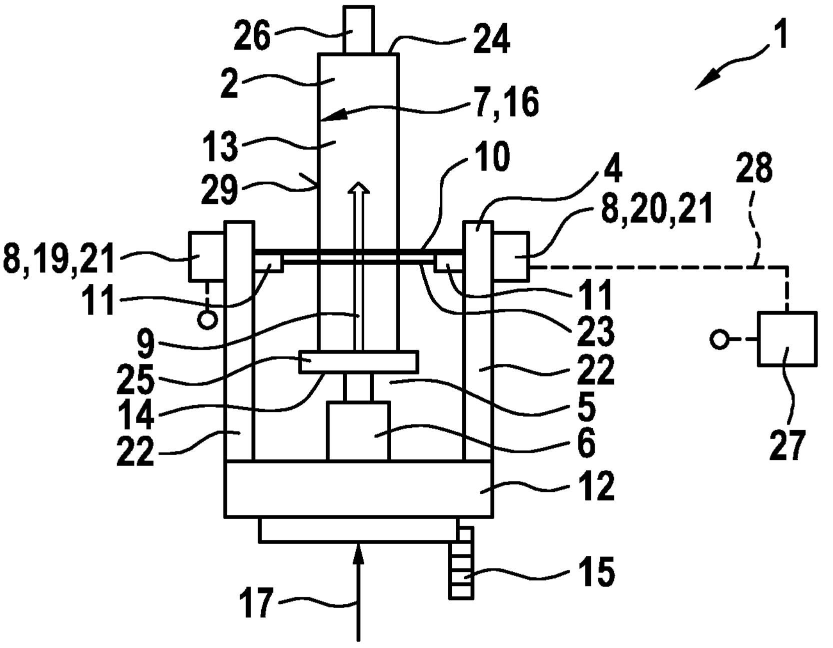
FIG. 3: shows a described device during a coating process.

FIG. 3 depicts a situation in which the object 2 is situated in the processing region 5; it occurs after the situation in FIG. 2, and the provision of silicone 9 by the silicone spray nozzle 6 takes place therein. The silicone 9 is injected through the open end 14 into the cylindrical body 13 of the object 2 in order to form the silicone coating 3 on the inner surface 16. Preferably, a guided movement 17 occurs in the meantime and brings about a uniform distribution of the silicone 9 on the inner surface 16. In the situation depicted in FIG. 3, the optical sensor 8 is able to identify the silicone 9 provided. The sensor components 21 of the optical sensor 8 and the outer surface 29 of the object 2 were cleaned in advance, or residual water possibly present there was removed. For this reason, the identification of the silicone 9 by the optical sensor 8 is no longer falsified by such residual water. The application of the silicone coating 3 made of the silicone 9 can be monitored closely.

Figure 4:
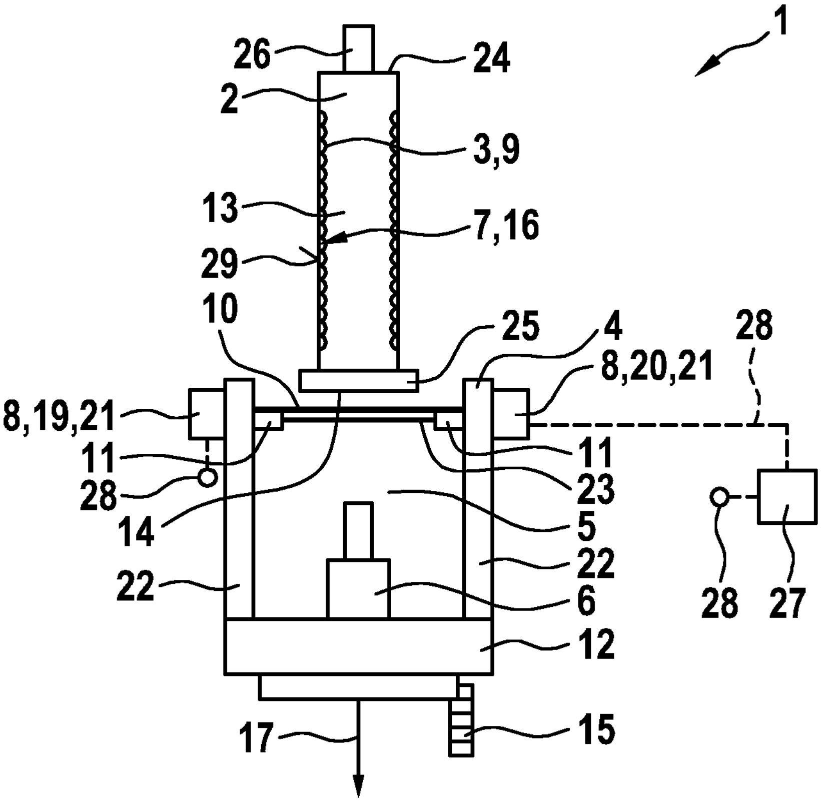
FIG. 4: shows a described device in a state following the completion of a coating process.

FIG. 4 shows a situation occurring after the situation depicted in FIG. 3. Here, the object 2 is moved out of the processing region 5 of the processing station 4 again. The silicone coating 3 made of silicone 9 has been applied in a surface region 7 of the inner surface 16 of the object 2.

Figure 5:
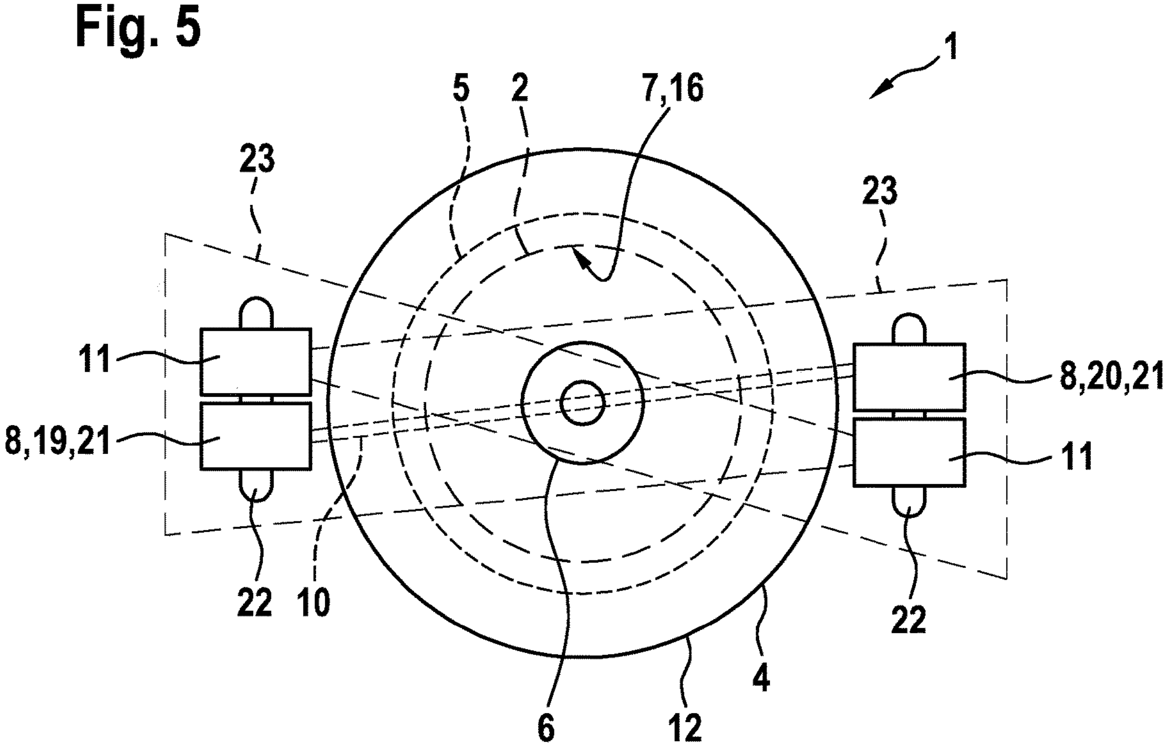
FIG. 5: shows an illustration of a described device in a view from above.

FIG. 5 shows a schematic illustration of the device 1 from above. The device 1 corresponds to the device 1 depicted in FIGS. 1 to 4. It is possible to identify the processing station 4 with the processing region 5, in which the object 2 is indicated schematically. From above, FIG. 5 also shows the silicone spray nozzle 6 on the base 12 of the processing station 4. The optical sensors 8 or the sensor components 21 of the optical sensor 8 are situated on mounts 22, in each case to the side of the processing station 4. The processing region 5 is situated between the optical sensors 8 or sensor components 21. One sensor component 21 of the optical sensor 8 is a sensor transmitter 19. A further sensor component 21 of the optical sensor 8 is a sensor receiver 20. An identification region 10 is situated between the sensor transmitter 19 and the sensor receiver 20, forms an (approximately) linear connection between the sensor transmitter 19 and the sensor receiver 20 and extends through the processing region 5. Silicone 9 applied to the object 2 can be identified by the optical sensor 8.

A compressed air nozzle 11 is also attached to each of the mounts 22. Compressed air can emerge from the compressed air nozzle 11. The compressed air nozzle 11 is constructed such that a flushing region 23 extends from it as a starting point, in which the compressed air emerging from the compressed air nozzle 11 flushes away contamination (or residual water in particular). In this case, the flushing region 23 is depicted conically in each case. By preference, the identification region 10 of the optical sensor 8 is located completely in the flushing region 23 such that contamination (or residual water in particular) in the identification region 10, which could interfere with the identification of silicone 9, can be effectively removed by the compressed air coming from the compressed air nozzles 11. By preference, the flushing regions 23 of the compressed air nozzles 11 also extend to the respectively opposing mounts 22, compressed air nozzles 11 and optical sensor components 21, and so the compressed air from the compressed air nozzles 11 also brings about cleaning/flushing of the opposing sensor components 21 when no object 2 to be coated is arranged in the processing region 5.

Figure 6:
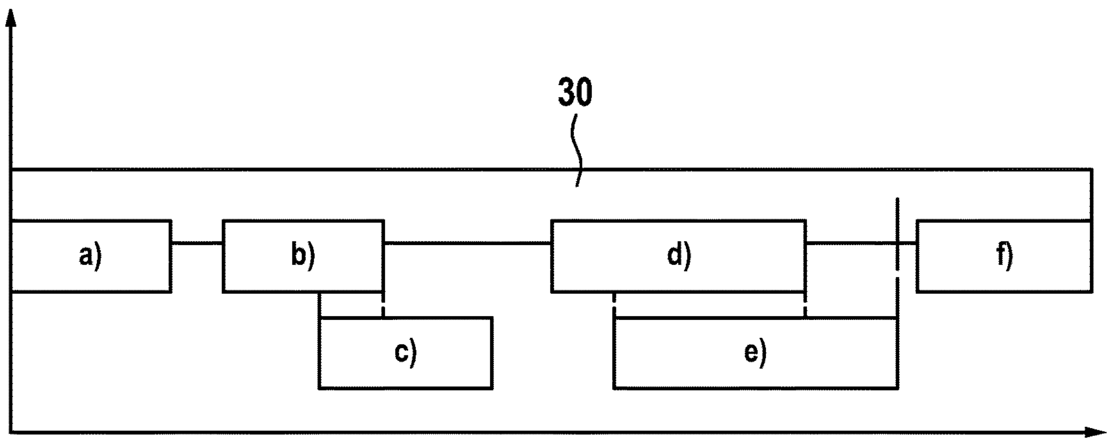
FIG. 6: shows a flowchart of the described method.

The procedure of the described method which is carried out by the described device 1 is additionally depicted very schematically in FIG. 6. The individual steps of the method are plotted schematically over a time axis. The compressed air provision 30 by the compressed air nozzles 11 is preferably implemented permanently during the entire execution of the described method. Step a) substantially corresponds to the situation depicted in FIG. 1. In this case, the compressed air is incident on the sensor components 21 of the optical sensor 8 in each case opposite to the compressed air nozzles 11. These sensor components 21 are cleaned here, or residual water is removed from these sensor components 21.

In step b), the object 2 is then introduced into the processing region 5. Then, the compressed air is also incident on the outer surface 29 of the object 2 while the object 2 is introduced into the processing region 5. The outer surface 29 of the object 2 is thus cleaned by the compressed air, or is freed from residual water. This takes place in step c). Step b) and step c) overlap in part because step c) starts automatically as a result of the introduction of the object 2 into the processing region 5. The situation during steps b) and c) is substantially depicted in FIG. 2.

The provision of silicone 9 by the silicone spray nozzle 6 in order to create the silicone coating 3 on the inner surface 16 of the object 2 is then implemented in step d). The quality of the silicone coating 3 is monitored in step e) simultaneously with the provision.

By preference, step d) is also followed by a step f), within the scope of which the object 2 is completely removed from the processing region 5 again and the device 1 is preferably put into the situation where it carries out steps a) to e) with a further object 2 in order to also coat this object 2. Steps a) to f) represent a work cycle of the device 1 for coating an object 2 with a silicone coating 3.

LIST OF REFERENCE SIGNS

1 Device
2 Object
3 Silicone coating
4 Processing station
5 Processing region
6 Silicone spray nozzle
7 Surface region
8 Optical sensor
9 Silicone
10 Identification region
11 Compressed air nozzle
12 Base
13 Cylindrical body
14 Open end
15 Guide means
16 Inner surface
17 Guided movement
18 Distance
19 Sensor transmitter
20 Sensor receiver
21 Sensor components
22 Mount
23 Flushing region
24 Closed end
25 Collar
26 Outlet
27 Controller
28 Data line
29 Outer surface
30 Compressed air provision

What is claimed is:

1. A device (1) for coating an object (2) with a silicone coating (3), comprising at least one processing station (4) with a processing region (5) for accommodating the object (2), at least one silicone spray nozzle (6) for applying silicone (9) to at least one surface region (7) of the object (2) such that a silicone coating (3) results, at least one optical sensor (8) for monitoring a quality of the silicone coating (3) by identifying silicone (9), the at least one optical sensor (8) having an identification region (10), in which the at least one optical sensor (8) can identify silicone (9) and which is aligned with the processing region (5), and at least one compressed air nozzle (11) directed at the identification region (10) of the at least one optical sensor (8) in order to flush the identification region (10) with compressed air.

2. The device (1) as claimed in claim 1, wherein the silicone spray nozzle (6) is arranged on a base (12) of the processing station (4) and directed upward such that silicone (9) is able to be sprayed into the processing region (5) from below by the silicone spray nozzle (6), the processing station (4) having guide means (15) for relative movement between the processing station (4) and the object (2) which are configured such that the silicone spray nozzle (6) is introducible into a cylindrical body (13) of the object (2) through an open end (14) in order to coat an inner surface (16) of the object (2) with silicone (9).

3. The device (1) as claimed in claim 1, wherein guide means (15) for introducing the object (2) into the processing station (4) are configured to bring about a guided movement (17) of the object (2) through the processing region (5), during which a distance (18) of the object (2) from a base (12) of the processing station (4) is changed continually during a process of spraying silicone (9) using the silicone spray nozzle (6) in order to bring about a uniform application of the silicone coating (3) on the at least one surface region (7) of the object (2).

4. The device (1) as claimed in claim 1, wherein the at least one optical sensor (8) is arranged above a base (12) of the processing station (4) to a side of the processing region (5), and the identification region (10) is aligned at least partly horizontally for identifying silicone (9) in the processing region (5).

5. The device (1) as claimed in claim 4, wherein the at least one optical sensor (8) has a two-part form with a sensor transmitter (19) and a sensor receiver (20), the processing region (5) being arranged between the sensor transmitter (19) and the sensor receiver (20) and the identification region (10) having a linear form from the sensor transmitter (19) to the sensor receiver (20) and extending through the processing region (5).

6. The device (1) as claimed in claim 1, wherein the at least one optical sensor (8) is configured to identify light at a wavelength in a range between 400 nanometers and 800 nanometers.

7. The device (1) as claimed in claim 1, wherein the at least one optical sensor (8) is configured to identify water components in silicone (9).

8. The device (1) as claimed in claim 1, wherein the at least one compressed air nozzle (11) is arranged above a base (12) of the processing station (4) to a side of the processing region (5) and directed at the identification region (10) of the at least one optical sensor (8).

9. The device (1) as claimed in claim 1, wherein at least one compressed air nozzle (11) is directed at at least one sensor component (21) of the at least one optical sensor (8).

10. The device (1) as claimed in claim 1, wherein at least two opposing sensor components (21) are arranged above a base (12) of the processing station (4) to a side of the processing region (5), the processing region (5) being arranged between the sensor components (21), and the device (1) having at least two compressed air nozzles (11), with a respective compressed air nozzle (11) being fastened to a mount (22) of one of the sensor components (21) and being directed at another one of the sensor components (21).

11. A method including the following steps:

a) providing the device (1) as claimed in claim 1;

b) cleaning the at least one optical sensor (8) using compressed air from the at least one compressed air nozzle (11);

c) introducing an object (2) into the processing region (5);

d) cleaning the object (2) using compressed air from the at least one compressed air nozzle (11);

e) applying the silicone coating (3) to at least one surface region (7) of the object (2), silicone (9) of the silicone coating (3) being provided by the at least one silicone spray nozzle (6); and f) monitoring a quality of the silicone coating (3) using the at least one optical sensor (8) by identifying silicone (9) during and/or after step e).

12. The method as claimed in claim 11, wherein water on the optical sensor (8) and on the object (2) is removed in step b) and step d) using the compressed air from the at least one compressed air nozzle (11) and wherein the at least one optical sensor (8) identifies water components in the silicone (9) in step f).

* * * * *